United States Patent [19]

Kem

[11] Patent Number: 4,818,774
[45] Date of Patent: Apr. 4, 1989

[54] ORGANOPHOSPHORUS COMPOUNDS

[75] Inventor: Kenneth M. Kem, Emmaus, Pa.

[73] Assignee: Occidental Chemical Corporation, Niagara Falls, N.Y.

[21] Appl. No.: 819,665

[22] Filed: Mar. 10, 1986

[51] Int. Cl.$^4$ ............ C08F 8/40; C07F 9/38; C07F 9/40
[52] U.S. Cl. .................. 521/31; 521/30; 558/161; 260/502.4 P
[58] Field of Search .............. 558/161; 260/502.4 P; 521/30, 31

[56] References Cited

U.S. PATENT DOCUMENTS 3,299,123  1/1967  Fitch et al. ................. 558/161
3,404,178 10/1968  Roy ........................ 260/502.4 P Primary Examiner—Anton H. Sutto
Attorney, Agent, or Firm—James F. Tao; William G. Gosz

[57] ABSTRACT

Polyvalent cations (e.g., U(IV), Fe(III) can be extracted from aqueous solution using novel organophosphorus compounds of the formulas:

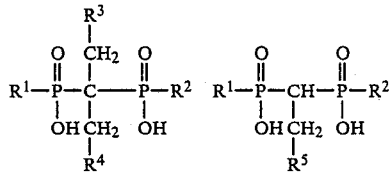

wherein $R^1$ and $R^2$ are the same or different and are selected from alkyl, alkoxyl, alkylaryl and alkylaryloxy groups having from 1 to 18 carbon atoms or hydroxyl;

$R^3$ is independently selected from substituted and unsubstituted alkyl and alkylaryl groups having 1 to about 18 carbon atoms or hydrogen;

$R^4$ is independently selected from alkyl and alkylaryl groups having 1 to about 18 carbon atoms; provided that the sum of the carbon atoms of the $R^1$, $R^2$, $R^3$ and $R^4$ groups is at least 15; and $R^5$ is independently selected from substituted and unsubstituted alkyl and alkylaryl groups having 1 to about 18 carbon atoms or a polymeric group; provided that the sum of the carbon atoms of the $R^1$, $R^2$ and $R^5$ groups is at least 16.

1 Claim, No Drawings

ORGANOPHOSPHORUS COMPOUNDS

BACKGROUND OF THE INVENTION

The invention involves novel compounds and compositions, which can be useful as extractants for the recovery of uranium from wet-process phosphoric acid (hereinafter, sometimes, "WPPA"), especially WPPA prepared by a hemi-hydrate route.

These compositions are multidentate ligands which are particularly suited for the formation of organic-soluble complexes of tetravalent uranium, that is U(IV) or $U^{+4}$, and in so doing can accomplish transfer of this ion from strong phosphoric acid solutions to organic solutions from which the U(IV) can conveniently be recovered.

The compounds can be expressed by the following formulas 1 and 2:

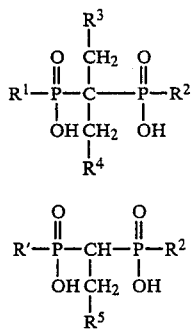

wherein
- $R^1$ and $R^2$ are the same or different and are selected from alkyl, alkoxyl, alkylaryl and alkylaryloxyl groups having from 1 to about 18 carbon atoms or hydroxyl;
- $R^3$ is independently selected from substituted or unsubstituted alkyl or alkylaryl groups having 1 to about 18 carbon atoms or hydrogen;
- $R^4$ is independently selected from alkyl or alkylaryl groups having 1 to about 18 carbon atoms; provided that the sum of carbon atoms of the $R^1$, $R^2$, $R^3$ and $R^4$ groups is at least 15; and
- $R^5$ is independently selected from substituted and unsubstituted alkyl or alkylaryl groups having 1 to about 18 carbon atoms or a polymeric group; provided that the sum of the carbon atoms of the $R^1$, $R^2$ and $R^5$ groups is at least 16.

Substituted alkyl and alkylaryl groups include alkyl and alkylaryl groups substituted with moieties, such as fluoro, chloro, bromo, iodo and hydroxyl groups, that are not deleteriously attacked during preparation of the compounds of formulas 1 and 2, and, preferably, not attacked by constituents when the compounds are used as extractants.

Useful for extracting U(IV) are compounds of formula 2 wherein $R^5$ is a polymeric group.

The novel compounds of this invention can be prepared by a method similar to that described by C. H. Roy in U.S. Pat. No. 3,422,021 in which 2-phenylethylene-1,1-diphosphonic acid was described along with substituted methylenediphosphonic acids as having utility as detergent builders. The compounds disclosed in U.S. Pat. No. 3,422,021 are not useful for the extraction of U(IV) from aqueous phosphoric acid.

Compositions similar to compounds of the general formulas 1 and 2 have been reported. For example, J. D. Spivak (U.S. Pat. Nos. 3,714,300 and 3,776,844) claims novel esters of general formula 3, which have utility as hindered phenol oxidation stabilizers.

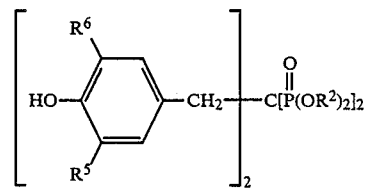

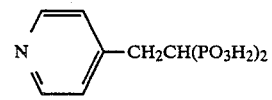

Similarly, the compound of formula 4 above is reported (Jpn. Kokai Tokkyo Koho 8,098,193) to have utility as a herbicide. Compounds of formulas 3 or 4 are not useful for extracting U(IV) from aqueous phosphoric acid.

Solvent extraction technology exists for the commercial recovery of uranium from conventional dihydrate phosphoric acid which has a concentration of about 28–30% $P_2O_5$. Thus, a mixture of di(2-ethyl-1-hexyl)-phosphoric acid, hereinafter, sometimes, "DEHPA", and tri(n-octyl)phosphine oxide, hereinafter, sometimes, "TOPO," in a molar ratio of about 4 to 1, is used as the extractants in a 2-cycle process used to extract uranium as U(IV) (F. J. Hurst, et al., *Ind. Eng. Chem, Process Des. Dev.*, 11(1), 122–8 (1972)). These extractants have the formulas:

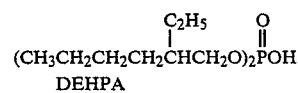
DEHPA

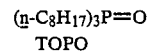
TOPO

Similarly, the mixture (commonly referred to as "pyroesters") produced by the reaction of alcohols of 8–10 carbon atoms with phosphorus pentoxide in a 2 to 1 molar ratio is used as the extractant in a one-cycle process for the extraction of U(IV) from dihydrate acid (D. A. Ellis, *The Recovery of Uranium from Industrial Phosphoric Acids by Solvent Extraction*, Report No. Dow-81, Dow Chem. Co. (1952)).

A mixture (commonly referred to as "OPAP") of nearly equimolar ratio of mono(4-t-octylphenyl)phosphoric acid (referred to as "MOPPA") and di(4-t-octylphenyl)phosphoric acid (referred to as "DOPPA") of formulas:

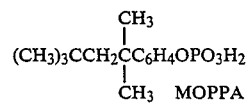

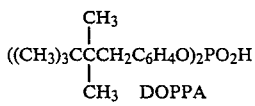

is used as the extractant in the first cycle of a two-cycle process to extract uranium as U(IV) from WPPA (F. J. Hurst and D. J. Crouse, *Ind. Eng. Chem. Process Des., Dev.*, 13(3), 287–91 (1974). The DEHPA-TOPO mixture described above is used as the extractant in the second cycle of this process to extract uranium as U(VI).

Pyrophosphate organic esters have high extraction coefficients for the removal of U(IV) from WPPA. However, pyrophosphate esters are not hydrolytically stable in WPPA. The compounds of formulas 1 and 2 have higher extraction coefficients for removal of U(IV) from WPPA and are hydrolytically stable in WPPA.

The difficulty of recovering uranium from more concentrated phosphoric acid solutions, such as the product of a hemihydrate WPPA process, has been described (J. J. Kohler, et al., *Recovery of Uranium from Hemihydrate Process Phosphoric Acid* (40 to 50% $P_2O_5$) *by Solvent Extraction*, paper presented at 180th Annular ACS Meeting Las Vegas, August, 1980).

Uranium is not presently recovered commercially from WPPA produced by a hemihydrate process (referred to herein as "hemihydrate WPPA"). Such acid is considerably more concentrated (36–50% $P_2O_5$) than WPPA produced by a conventional dihydrate process (26–31% $P_2O_5$).

While uranium can be recovered by any of the above referenced processes from dihydrate WPPA, uranium is difficult to recover from hemihydrate WPPA. The extractants used in these processes have prohibitively poor extractant strength for use with the more concentrated WPPA (e.g., hemihydrate WPPA), or have precipitation, solubility, or fouling problems when used to extract more concentrated WPPA, or are hydrolytically unstable and are degraded and lost during extraction in more concentrated WPPA. The novel compounds of the present invention present a great improvement over such prior art extractants, particularly for use with more concentrated WPPA, such as, hemihydrate WPPA.

Additional information regarding uranium recovery processes is set forth in: *Phosphorus & Potassium* (99), 31–3, (1979); A. P. Kouloheris, *Chem. Eng.*, Aug. 11, 1980, pp. 82–4; B. F. Greek, O. W. Allen and D. E. Tynan, *Ind. Eng. Chem.*, 49 (4), 628–38 (1957).

THE SUMMARY OF THE INVENTION

The invention involves chemical compounds having the general formulas:

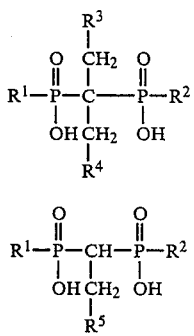

wherein
$R^1$ and $R^2$ are the same or different and are selected from alkyl, alkoxyl, alkylaryl and alkylaryloxyl groups having from 1 to 18 carbon atoms or hydroxyl;

$R^3$ is independently selected from substituted and unsubstituted alkyl and alkylaryl groups having 1 to about 18 carbon atoms or hydrogen;

$R^4$ is independently selected from alkyl and alkylaryl groups having 1 to about 18 carbon atoms; provided that the sum of the carbon atoms of the $R^1$, $R^2$, $R^3$ and $R^4$ groups is at least 15;

$R^5$ is independently selected from substituted and unsubstituted alkyl and alkylaryl groups having 1 o about 18 carbon atoms or a polymeric group; provided that the sum of the carbon atoms of the $R^1$, $R^2$ and $R^5$ groups is at least 16.

In order to possess sufficient hydrophobic character for extracting polyvalent cations from aqueous media and effect the transfer thereto to an organic phase, the $R^1$, $R^2$, $R^3$, $R^4$ and $R^5$ groups of the compounds of formulas 1 and 2 are selected such that the total or aggregate number of carbon atoms, combined, of the $R^1$, $R^2$, $R^3$ and $R^4$ groups in the compounds of formula 1 and of the $R^1$, $R^2$, and $R^5$ groups in the compounds of formula 2 are at least 16. The compounds include multidentate ligands useful as a selective extractant for transferring a polyvalent cation (e.g., Fe(III), U(IV)) from an aqueous phase to an organic phase. For example, the compounds can be used as a selective extractant for transferring U(IV) from solution in an aqueous phosphoric acid to an organic phase. The compouns of formulas 1 and 2 are useful as a substantially quantitative extractant for transferring U(IV) from hemihydrate WPPA to an organic phase solution.

Another preferred class of compounds are the compounds of formulas 1 and 2 wherein $R^1$ and $R^2$ are hydroxyl. Extractant compositions can comprise mixtures of two or more compounds of formulas 1 and/or 2, such as a mixture of one compound wherein $R^3$ is alkyl or alkylaryl.

Also preferred are compounds of formulas 1 and 2 wherein at least one of $R^1$, $R^2$, $R^3$, $R^4$ and $R^5$ is a branched alkyl phenyl group. Such as, for example, 2-(dodecylphenyl)ethylene-1,1-diphosphonic acid, 1,3-di(dodecylphenyl)propylene-2,2-diphospnic acid, 2-(4-t-butylphenyl)-ethylene-1,1-diphosphonic acid and 1,3-di(4-t-butylphenyl)propylene-2,2-diphosphonic acid.

Also useful are admixtures of such compounds of formulas 1 and 2 with at least one neutral organophosphorus compound, e.g., tri(n-octyl)phosphine oxide. Said mixtures have been found to be superior extractants for extraction of a polyvalent metal cation from an aqueous medium to an organic phase compared to the neutral organophosphorus compound alone.

The compounds of formula 2 can be made as solids when $R^5$ comprises a polymeric group. Such as, for example, the compounds of formula 2 wherein $R^5$ comprises a polystyrene, polyarylether sulfone, or polyphenylene oxide polymeric group.

The compounds of formula 2 wherein $R^5$ is a polymeric group, such as polystyrene, can be used to recover uranium values [particularly U(IV)] from WPPA. In this embodiment, the extractant is immobilized onto the polymer backbone and the mode of separation is solid-liquid ion exchange rather than liquid-liquid ion exchange.

DETAILED DESCRIPTION OF THE INVENTION

In an extraction process using the novel compounds and compositions of the invention, hemihydrate strength phosphoric acid (36–50 weight % $P_2O_5$) containing uranium in either tetravalent or hexavalent form or mixtures thereof (but preferably tetravalent) is contacted, in a countercurrent manner, in an extractant stage employing suitable equipment (such as mixer-settlers, pulse columns, and the like) with an immiscible organic extract phase containing one or more compounds of formulas 1 and 2 in a hydrocarbon diluent. Optionally, the extractant can contain synergists, modifiers and other extractants to extract the uranium values more or less completely into the organic phase. After separating the extractant phase from the barren phosphoric acid raffinate, the phosphoric acid may be further processed into merchant grade acid, chemical fertilizers, or the like.

The uranium-loaded extractant phase may be stripped in a stripping stage using contacting equipment (such as mixer-settlers, columns, and the like). For example, the extractant phase can be contacted countercurrently with an aqueous stripping phase containing hydrofluoric acid in concentration of 3 to 50%, preferably 10–20%, to strip and precipitate uranium as the insoluble uranium tetrafluoride ($UF_4$). The barren extractant after stripping and separation of the aqueous stripping phase can be recycled to the extraction stage to recover additional uranium from hemihydrate strength phosphoric acid. The aqueous stripping phase, a slurry of $UF_4$ solids in dilute hydrofluoric acid, can be delivered to a solid liquid phase separator (such as a filter, centrifuge, or settler) to separate "green cake" ($UF_4$) from the liquid phase. The liquid phase containing hydrofluoric acid can be recycled to the stripping stage and fortified with makeup hydrofluoric acid. The damp green cake can be dried in a dryer and marketed directly or further purified prior to marketing by techniques well known to those skilled in the art, such as the Gardinier process using a second cycle extraction with tributylphosphate from a nitrate solution.

Iron Removal from WPPA

The deleterious effects of the presence of iron in both merchant grade phosphoric acids and superphosphoric acids may become a more serious problem in the future than it is at present when high iron content phosphate rock is converted to WPPA.

Many of the prior art extractants described above are fouled by Fe(III), ferric iron, because the Fe(III) forms insoluble salts with such extractants. The compounds of formulas 1 and 2 do not form insoluble salts with Fe(III), and some of the compounds are effective Fe(III) extractants.

Iron can be removed from WPPA by solvent extraction. Compounds of formula 1 wherein $R^1$ and $R^2$ each are hydroxyl and $R^3$ and $R^4$ are each alkylaryl of from 10 to 18 carbon atoms exhibited extraction coefficients for Fe(III) ranging from 0.77 to 1.65.

Another analog compound of formula 1 wherein $R^1$ and $R^2$ are each hydroxyl and $R^3$ and $R^4$ are each n-decyl, exhibits outstanding U(IV) and attractive Fe(III) extraction coefficients (see Table I). Another useful analog compound of formula 1 wherein $R^1$ and $R^2$ are each hydroxyl and $R^3$ and $R^4$ are each isododecyl ($R=i-C_{12}H_{25}$) exhibits low extractant loss.

TABLE 1

Extraction Coefficients of Pentacosane-13,13-diphosphonic acid (PCDPA) for Iron and Uranium, Isopar M Solvent, 40° C. 1:1 phase Ratio.

| EXTRACTANT | FEED | $D_{Fe(III)}$ | $D_{U(VI)}$ |
|---|---|---|---|
| 0.5 M PCDPA | Oxidized | 1.91 | 1.03 |
|  | Reduced | 0.28 | 260.00 |
| 0.5 M PCDPA | Oxidized | 1.98 | 2.85 |
| +0.125 M TOPO | Reduced | 0.17 | 55.80 |
| 0.2 M OPAP | Reduced | — | 1.70 |
| 0.5 M DEHPA | Oxidized | — | 1.04 |

ILLUSTRATIVE EXAMPLES

EXAMPLE 1

Step 1. Alkylation of Tetraisopropylmethylenediphosphonate

Potassium hydride (KH) was obtained from Aldrich Chemical Company in the form of an oil dispersion. It was freed from this dispersion by the produce of C. A. Brown, *J. Org. Chem.*, 39, 3913 (1974). In this procedure, dry tetrahydrofuran (THF) was added to the dispersion under a $N_2$ atmosphere and the mixture stirred briefly and allowed to settle. The THF-oil solution was removed by syringe to where the remaining solution just covered the KH. The procedure was repeated two additional times to produce a nearly oil-free dispersion of KH in THF. Other suitable strong anhydrous bases, such as sodium metal, can be employed.

To this KH mixture, under $N_2$ at 0° C., was added dropwise with stirring an equimolar amount of tetraisopropylmethylenediphosphonate (TPMDP), and THF. The evolution of hydrogen was evident. When it subsided (approximately one hour) the reaction temperature was adjusted to 25° C. and an equimolar amount of an alkylating agent, $R^4CH_2X$, in THF was added dropwise over a one-hour period. When the addition was complete, the mixture was refluxed for one hour. The mixture was allowed to cool, then filtered. The experimental scheme above can be illustrated by the following equation:

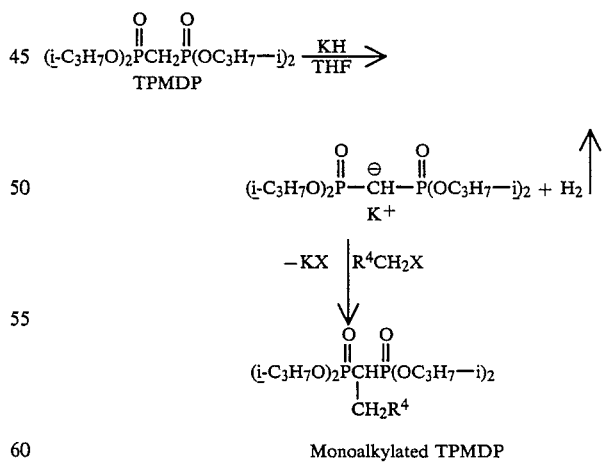

Monoalkylated TPMDP

Step II. Alkylation of Monoalkylated TPMDP

The filtrate obtained above in Step I was divided into equal portions A and B. Filtrate portion A was set aside for later hydrolysis. Filtrate portion B was further alkylated by reaction with an equimolar amount of KH at 0° C., as described above, followed by reaction with another equimolar portion of an alkylating agent, R³CH₂X, at 25° C., as described above, and followed by refluxing for one hour. After cooling and filtering, the filtrate obtained contained the dialkylated TPMDP as illustrated by the following equation:

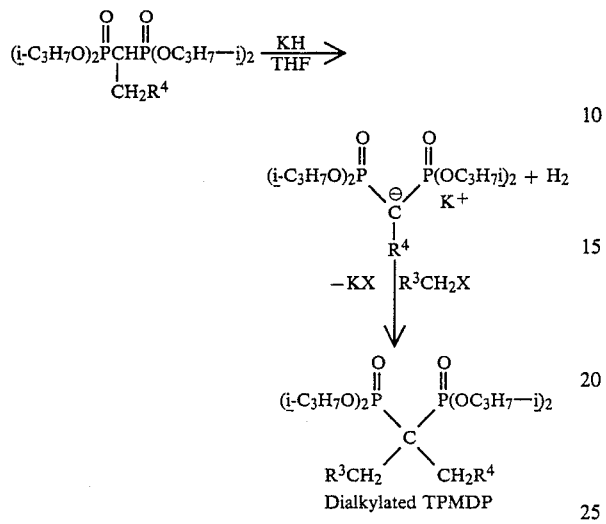

With respect to alkylating agents R³CH₂X and R⁴CH₂X, R³ and R⁴ are substituted or unsubstituted alkyl or alkylaryl groups of from 1 to about 18 carbon atoms, and X is a leaving group such as chloro, bromo, iodo, arylsulfonate, alkylsulfonate or alkylsulfate.

EXAMPLE 2

Cleavage of Alkylated Tetraisopropylmethylenediphosphonates

The filtrate solutions as obtained in Steps I or II (mono- or dialkylated TPMDP, respectively) in THF were evaporated in vacuo and the residue dissolved in chlorobenzene, which was refluxed with 47% hydrobromic acid for five hours with vigorous stirring. The mixture was cooled, the phases separated, and the organic layer washed with deionized water, followed by washing with a saturated sodium chloride solution. The organic layer was dried over anhydrous sodium sulfate, filtered and evaporated in vacuo to yield the alkylated methylenediphosphonic acids (as illustrated in the following equations:)

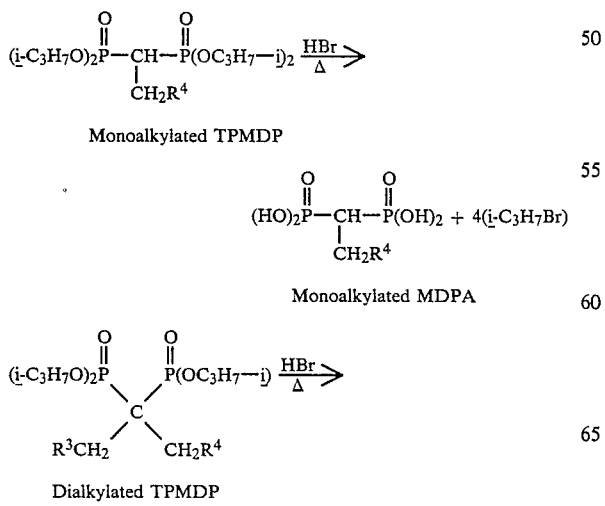

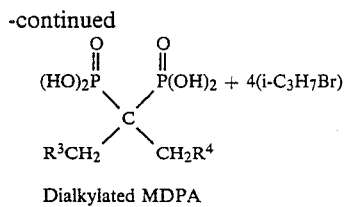

Dialkylated MDPA

The Arbuzov ester cleavage of the dialkylated TPMDP generally produces a product mixture consisting of a solid and an oil in about 1:4 ratio. Filtration of the solid is performed by suction. After washing and recrystallizing the solid from pentane, a pure comound was obtained which can be characterized by ¹H and ³¹P NMR to be the symmetrical half-ester of the following formula:

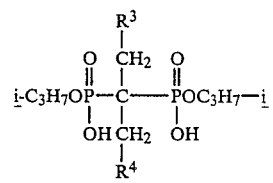

These are novel compounds and are useful extractants for polyvalent metals.

The filtrate oil portion of the product (dialkylated MDPA) is the composition evaluated in the further examples. The oil contains a mixture of the diacids, mono esters, symmetrical diesters, unsymmetrical diesters and triesters of the monoalkylated MDPA and dialkylated MDPA. This mixture results from the non-quantitative nature of the Arbuzov reaction. The diacid, mono ester and symmetrical diester are the preferred compositions for extraction of polyvalent metals.

Monoalkylated TPMDP's of the following formula are prepared in accordance with the process of Step I, of Example 1 using alkylating agent R⁵CH₂X in place of R⁴CH₂X:

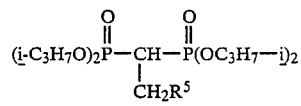

Wherein R⁵ is as defined herein.

Useful monoalkylated MDPA's of the following formulas can be prepared from the above monoalkylated TPMDP's by the process of Example 2:

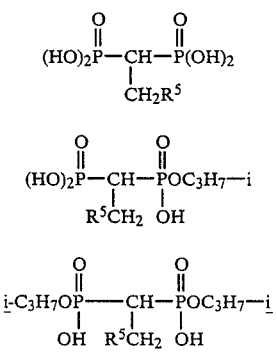

-continued

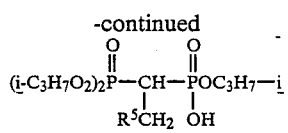

EXAMPLE 3

The product of the reaction of tetraisopropylmethylenediphosphonate with an equimolar amount of sodium and dodecylbenzyl chloride followed by hydrolysis was found by $^{31}P$ NMR to be a mixture of 2-(dodecylphenyl)ethylene-1,1-diphosphonic acid (a compound of formula 2 wherein $R^5=C_{12}H_{25}C_6H_4$, $R^1=R^2=OH$) and 1,3-di(dodecylphenyl)propylene-2,2-diphosphonic acid (the compound of formula 1 wherein $R^3=R^4=C_{12}H_{25}C_6H_4$, $R^1=R^2=OH$). The mixture was predominantly the former and is designated DPEDPA.

Similarly, the product of the reaction of tetraisopropylmethylenediphosphonate with a two-fold molar amount of sodium and dodecylbenzyl chloride followed by hydrolysis is found by $^{31}P$ NMR to be a mixture of the same two compounds described above. The mixture was predominantly the latter compound and is designated DDPPDPA.

EXAMPLE 4

The product of the reaction of tetraisopropylmethylenediphosphonate with a two-fold molar amount of potassium hydride and 4-t-butylbenzyl chloride followed by hydrolysis produces a product which consists of a solid and an oil in about a 1:4 ratio. Filtration of the solid produced an oil filtrate which was characterized by $^1H$ and $^{31}P$ NMR to be a mixture of 2-(4-t-butylphenyl)ethylene-1,1-diphosphonic acid (a compound of formula 2 wherein $R^5=4\text{-}t\text{-}C_4H_9C_6H_4$, $R^1=R^2=OH$) and 1,3-di(4-t-butylphenyl)propylene-2,2-diphosphonic acid (a compound of formula 4 wherein, $R^3=R^4=4\text{-}t\text{-}C_4H_9C_6H_4$, $R^1=R^2=OH$). The mixture was predominantly the latter compound and is designated DBPPDPA. Recrystallization of the filtered solid from pentane afforded sym-di-i-propyl-1,3-di(4-t-butylphenyl)propylene-2,2-diphosphonic acid which melted at 214°–5° and had the following structure as evidenced by $^{31}P$ and $^1H$ NMR:

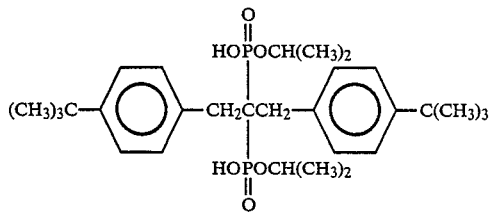

EXAMPLE 5

By essentially the same process as described in Example 4, pentacosane-13,13-diphosphonic acid (PCDPA) (the compound of formula 1, wherein $R^1=R^2=OH$ and $R^3=R^4=n\text{-}C_{11}H_{23}$) was prepared by employing n-dodecyl chloride in place of 4-t-butylbenzyl chloride.

EXAMPLE 6

By essentially the same process as described in Example 4, di(i-tridecyl)methylenediphosphonate acid (the compound of formula 1, wherein $R^1=R^2=OH$ and $R^3=R^4=i\text{-}C_{12}H_{25}$) was prepared by employing i-tridecyl chloride in place of 4-t-butylbenzyl chloride.

EXAMPLE 7

The following evaluation procedure was utilized to compare these novel extractants, and mixtures thereof with neutral organophosphorus extractants, to conventional extractants for extractant strength:

Extraction of Uranium from Wet-Process Phosphoric Acid

Shake tests were performed using "green" hemihydrate WPPA (43% $P_2O_5$) produced in Florida by the "OXY Hemihydrate Process" which, after pretreatment with activated charcoal (by the procedure described in B. D. Wells, *Treatment of Wet Process Phosphoric Acid with Activated Carbon*, paper presented at the ACS National Meeting, Las Vegas, Nev., August, 1980), contained 40 mg/l uranium. The extractant composition being tested was dissolved in Isopar M (a deodorized kerosene product of Exxon) to produce the solution concentrations shown in Table II.

Florida "black" phosphoric acid was pretreated with "Calgon" activated charcoal at ambient temperatures to remove organic impurities and produce a "green" acid.

A portion of the green acid was reduced with iron nails to 110–130 mV (measured with a platinum redox electrode) and another portion was oxidized with chlorate to 1100–115 mV.

A 1:1 volume ratio mixture was made of a sample of each such reacted (i.e. reduced oxidized) acid, "green" acid and the extractant solution. The sample mixtures were maintained at 40° C. by means of a temperature bath.

The extraction runs were made with the reduced and oxidized acids. The two-phase 1:1 ratio mixtures at 40° C. were shaken for five minutes and allowed to separate. Each phase was analyzed for uranium by neutron activation to calculate the extraction coefficients from reduced acid ($D_{U(IV)}$) and from oxidized acid ($D_{U(VI)}$).

The table below compares the extraction coefficients of these novel extractants with those of the prior art. If these extraction coefficients are significantly changed after refluxing the extractant overnight in water, the new value is recorded in parentheses. Particularly evident is the hydrolytic instability of the pyroester, di(2-ethyl-1-hexyl)pyrophosphoric acid (DEHPPA).

TABLE II

| Extraction Coefficients for Uranium from Decolorized Oxy Hemiacid (43% $P_2O_5$): 1:1 Phase Ratio in Isopar M; 40° C. | | | |
|---|---|---|---|
| EXTRACTANT | CONC.(M) | $D_{U(IV)}$ | $D_{U(VI)}$ |
| DEHPA | 0.5 | 0.013 | 0.625 |
| TOPO | 0.125 | | |
| OPAP | 0.2 | 2.10 | 0.021 |
| | | (1.58) | (0.011) |
| DEHPPA | 0.5 | 77.5 | 9.37 |
| | | (0.047) | (0.141) |
| DPEDPA | 0.5 | 384 | 0.268 |
| DPEDPA | 0.5 | 46.0 | 0.78 |
| TOPO | 0.125 | | |
| DDPPDPA | 0.5 | 3140 | 0.35 |
| DDPPDPA | 0.5 | 15.7 | 0.99 |
| TOPO | 0.125 | | |
| DBPPDPA | 0.5 | * | 2.62 |
| DBPPDPA | 0.5 | 237 | 3.12 |
| TOPO | 0.125 | | |

*No uranium could be detected in the raffinate; extraaction was quantitative.

EXAMPLE 8

Using the procedures of Example 1, a monoalkylated TPMDP was prepared in which R⁴X comprised a crosslinked chromomethylated polystyrene resin. Following hydrolysis (as in Example 1), further resins were obtained having the specifications shown in Table III:

TABLE III
Properties and Reactivity of TPMDP-Resins

| Starting Resin | Chloromethyl-<br>ated Resin A | Chloromethyl-<br>ated Resin B |
|---|---|---|
| Chlororethylation (Meq/g Cl) | 1.25 | 4.2 |
| Crosslinking (wt % DVB) | 2 | 1 |
| Bead Size (mesh) | 100–200 | 200–400 |
| Conversion to monoalkylated TPMDP (mole %)* | 10 | 60 |

*Estimated by consumption of TPMDP

The Resin B product swells to about three times its dry volume in tetrahydrofuran which facilitates transport of reagents to the reactive sites from aqueous (including strongly acidic) media.

Following the procedures of Examples 1 and 2, dialkylated methylenediphosphinic acids can be prepared as shown in analogous Examples 9 and 10.

EXAMPLE 9

Step 1. Alkylation of Methylenediphosphinates

A procedure for alkylating methylenediphosphinates can be illustrated by the following equations:

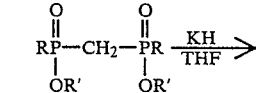

Methylenediphosphinate

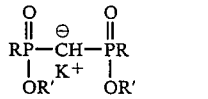

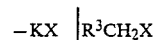

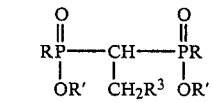

Monoalkylated Methylenediphosphinate

Step 2. Alkylation of Monoalkylated Methylenediphosphinates

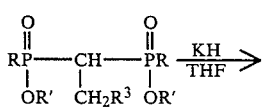

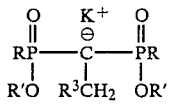

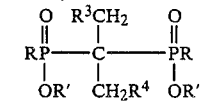

Dialkylated Methylenediphosphinate

EXAMPLE 10

Cleavage of Alkylated Methylenediphosphinates

Cleavage of the alkylated methylenediphosphinates of Example 9 can be illustrated by the following equations:

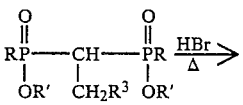

Monoalkylated
Methylenediphosphinate

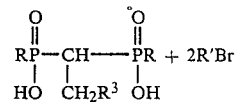

Monoalkylated
Methylenediphosphinicacid

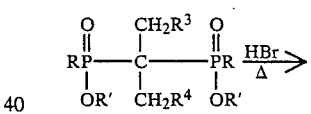

Dialkylated
Methylenediphosphinate

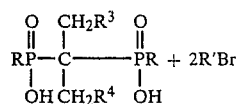

Dialkylated
Methylenediphosphinic Acid

What is claimed is:
1. As compositions of matter, chemical compounds having the general formula

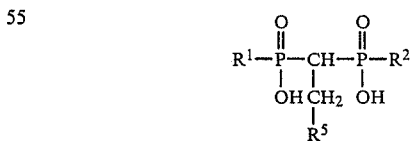

wherein R¹ and R² can be the same or different and are selected from alkyl, alkoxyl, alkylaryl and alkylaryloxyl groups having 1 to about 18 carbon atoms or hydroxy; and R⁵ is a polymer radical selected from the group consisting of polystyrene, polyphenylene ether and polyarylether sulfone, provided that the sum of the carbon atoms of the R¹, R² and R⁵ groups is at least 16.

* * * * *